US008597309B2

(12) United States Patent
Stafford

(10) Patent No.: US 8,597,309 B2

(45) **Date of Patent: *Dec. 3, 2013**

(54) SUTURING DEVICE WITH SPLIT ARM AND METHOD OF SUTURING TISSUE

(75) Inventor: Joshua Stafford, Menlo Park, CA (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/615,530

(22) Filed: Sep. 13, 2012

(65) Prior Publication Data

US 2013/0006277 A1 Jan. 3, 2013

Related U.S. Application Data

(60) Continuation of application No. 12/247,012, filed on Oct. 7, 2008, now Pat. No. 8,419,753, which is a division of application No. 10/746,210, filed on Dec. 23, 2003, now Pat. No. 7,449,024.

(51) Int. Cl.
*A61B 17/04* (2006.01)
*A61B 17/12* (2006.01)

(52) U.S. Cl.
USPC .......................................... 606/144; 606/139

(58) Field of Classification Search
USPC ......................................... 606/139, 144–148
See application file for complete search history.

(56) References Cited

U.S. PATENT DOCUMENTS

| | | | |
|---|---|---|---|
| 312,408 | A | 2/1885 | Wackerhagen |
| 597,165 | A | 1/1898 | Hall |
| 659,422 | A | 10/1900 | Shidler |
| 989,231 | A | 4/1911 | Davis |
| 1,574,362 | A | 9/1922 | Callahan |
| 1,625,602 | A | 4/1927 | Gould et al. |
| 1,940,351 | A | 3/1933 | Howard |
| 2,012,776 | A | 8/1935 | Roeder |
| 2,131,321 | A | 10/1937 | Hart |
| 2,127,903 | A | 8/1938 | Bowden |
| 2,371,978 | A | 3/1945 | Perham |
| 2,397,823 | A | 4/1946 | Walter |
| RE22,857 | E | 3/1947 | Ogburn |
| 2,595,086 | A | 11/1948 | Larzelere |
| 2,588,589 | A | 3/1952 | Tauber |
| 2,646,045 | A | 7/1953 | Priestley |

(Continued)

FOREIGN PATENT DOCUMENTS

| | | |
|---|---|---|
| DE | 912619 | 5/1954 |
| DE | 4210724 | 7/1993 |

(Continued)

OTHER PUBLICATIONS

U.S. Appl. No. 12/950,338, mailed Nov. 14, 2012, Issue Notification.

(Continued)

*Primary Examiner* — Gary Jackson

*Assistant Examiner* — Michael Mendoza

(74) *Attorney, Agent, or Firm* — Workman Nydegger; Randy Shen

(57) ABSTRACT

A device for suturing an opening in a tissue, having an elongated shaft, at least two arms movable to a deployed positioning which the arms are non-perpendicular to the shaft, the arms having needle receiving portions; and needles advanceable longitudinally along the shaft toward the needle receiving portions, the needles exiting through side walls of the shaft at a location proximal to the arms.

20 Claims, 7 Drawing Sheets

(56) References Cited

U.S. PATENT DOCUMENTS 2,692,599 A 10/1954 Creelman
2,941,489 A 6/1960 Fischbein
2,959,172 A 11/1960 Held
3,033,156 A 5/1962 Verlish
3,104,666 A 9/1963 Hale et al.
3,197,102 A 7/1965 Bates et al.
3,359,983 A 12/1967 Northey
3,413,397 A 11/1968 Bierbaum et al.
3,422,181 A 1/1969 Chirgwin, Jr.
3,470,875 A 10/1969 Johnson
3,485,234 A 12/1969 Stevens
3,587,115 A 6/1971 Shiley
3,630,205 A 12/1971 Listner
3,653,388 A 4/1972 Tenckhoff
3,665,926 A 5/1972 Flores
3,776,237 A 12/1973 Hill et al.
3,802,438 A 4/1974 Wolvek
3,820,544 A 6/1974 Semm
3,840,017 A 10/1974 Violante
3,874,388 A 4/1975 King et al.
3,878,848 A 4/1975 Hiebert
3,918,455 A 11/1975 Coplan
3,926,194 A 12/1975 Greenberg et al.
3,939,820 A 2/1976 Grayzel
3,985,138 A 10/1976 Jarvik
4,018,228 A 4/1977 Goosen
4,069,825 A 1/1978 Akiyama
4,109,658 A 8/1978 Hughes
4,128,100 A 12/1978 Wendorff
4,135,623 A 1/1979 Thyen
4,161,951 A 7/1979 Scanlan, Jr.
4,168,073 A 9/1979 LaRue
4,182,339 A 1/1980 Hardy, Jr.
4,185,636 A 1/1980 Gabbay et al.
4,216,776 A 8/1980 Downie et al.
4,217,665 A 8/1980 Bex et al.
4,235,177 A 11/1980 Arbuckle
4,235,238 A 11/1980 Ogiu et al.
4,316,469 A 2/1982 Kapitanov
4,317,445 A 3/1982 Robinson
4,411,654 A 10/1983 Boarini et al.
4,412,832 A 11/1983 Kling et al.
4,437,465 A 3/1984 Nomoto et al.
4,469,101 A 9/1984 Coleman et al.
4,492,229 A 1/1985 Grunwald
4,493,323 A 1/1985 Albright et al.
4,553,543 A 11/1985 Amarasinghe
4,586,614 A 5/1986 Ger
4,587,969 A 5/1986 Gillis
4,596,559 A 6/1986 Fleishhacker
4,610,248 A 9/1986 Rosenberg
4,629,450 A 12/1986 Suzuki et al.
4,651,733 A 3/1987 Mobin-Uddin
4,655,211 A 4/1987 Sakamoto et al.
4,702,250 A 10/1987 Orvil et al.
4,723,549 A 2/1988 Wholey et al.
4,738,666 A 4/1988 Fuqua
4,744,364 A 5/1988 Kensey
4,748,982 A 6/1988 Horzewski et al.
4,782,954 A 11/1988 Reynolds
4,803,984 A 2/1989 Narayanan et al.
4,836,205 A 6/1989 Barrett
4,845,851 A 7/1989 Warthen
4,848,341 A 7/1989 Ahmad
4,852,568 A 8/1989 Kensey
4,890,612 A 1/1990 Kensey
4,898,155 A 2/1990 Ovil et al.
4,911,164 A 3/1990 Roth
4,917,089 A 4/1990 Sideris
4,926,860 A 5/1990 Stice et al.
4,929,246 A 5/1990 Sinofsky
4,935,027 A 6/1990 Yo on
4,950,285 A 8/1990 Wilk
4,957,498 A 9/1990 Caspari et al.
4,966,600 A 10/1990 Songer et al.
4,981,149 A 1/1991 Yoon et al.
4,983,168 A 1/1991 Moorehead
4,984,581 A 1/1991 Stice
5,002,563 A 3/1991 Pyka et al.
5,009,643 A 4/1991 Reich et al.
5,021,059 A 6/1991 Kensey et al.
5,037,433 A 8/1991 Wilk et al.
5,041,129 A 8/1991 Hayhurst et al.
5,047,039 A 9/1991 Avant et al.
5,059,201 A 10/1991 Asnis
5,061,274 A 10/1991 Kensey
5,074,874 A 12/1991 Yoon et al.
5,078,721 A 1/1992 McKeating
5,080,664 A 1/1992 Jain
5,100,419 A 3/1992 Ehlers
5,100,422 A 3/1992 Berguer et al.
5,100,432 A 3/1992 Matsutani
5,108,421 A 4/1992 Fowler
5,109,780 A 5/1992 Slouf et al.
5,129,882 A 7/1992 Weldon et al.
5,129,912 A 7/1992 Noda et al.
5,129,913 A 7/1992 Ruppert
5,144,961 A 9/1992 Chen et al.
5,147,373 A 9/1992 Ferzli
5,156,788 A 10/1992 Chesterfield et al.
5,160,339 A 11/1992 Chen et al.
5,163,946 A 11/1992 Li
5,169,041 A 12/1992 Tan
5,171,251 A 12/1992 Bregen et al.
5,176,691 A 1/1993 Pierce
5,178,629 A 1/1993 Kammerer
5,192,294 A 3/1993 Blake, III
5,192,301 A 3/1993 Kamiya et al.
5,192,302 A 3/1993 Kensey et al.
5,201,744 A 4/1993 Jones
5,207,703 A 5/1993 Jain
5,211,650 A 5/1993 Noda
5,217,470 A 6/1993 Weston
5,217,485 A 6/1993 Liv et al.
5,219,358 A 6/1993 Bendel et al.
5,222,974 A 6/1993 Kensey et al.
5,234,443 A 8/1993 Phan et al.
5,234,445 A 8/1993 Walker et al.
5,237,985 A 8/1993 Hodgson et al.
5,242,427 A 9/1993 Bilweis
5,250,033 A 10/1993 Evans et al.
5,250,053 A 10/1993 Snyder
5,250,054 A 10/1993 Li
5,254,105 A 10/1993 Haaga
5,254,113 A 10/1993 Wilk
5,254,126 A 10/1993 Filipi et al.
5,258,003 A 11/1993 Ciaglia et al.
5,259,846 A 11/1993 Granger et al.
5,275,616 A 1/1994 Fowler
5,279,311 A 1/1994 Snyder
5,281,236 A 1/1994 Bagnato et al.
5,281,237 A 1/1994 Gimpelson
5,284,485 A 2/1994 Kammerer et al.
5,285,945 A 2/1994 Brinkerhoff et al.
5,289,963 A 3/1994 McGarry et al.
5,290,284 A 3/1994 Adair
5,290,297 A 3/1994 Phillips
5,290,310 A 3/1994 Makower et al.
5,292,309 A 3/1994 Van Tassel et al.
5,292,327 A 3/1994 Dodd et al.
5,292,332 A 3/1994 Lee
5,293,881 A 3/1994 Green et al.
5,295,993 A 3/1994 Green
5,300,085 A 4/1994 Yock
5,304,184 A 4/1994 Hathaway et al.
5,304,185 A 4/1994 Taylor
5,306,254 A 4/1994 Nash et al.
5,312,024 A 5/1994 Grant et al.
5,312,423 A 5/1994 Rosenbluth et al.
5,318,578 A 6/1994 Hasson
5,320,629 A 6/1994 Noda et al.
5,320,632 A 6/1994 Heidmueller
5,330,445 A 7/1994 Haaga
5,330,491 A 7/1994 Walker et al.

(56) References Cited

U.S. PATENT DOCUMENTS 5,334,217 A 8/1994 Das
5,336,229 A 8/1994 Noda
5,336,230 A 8/1994 Leichtling et al.
5,336,231 A 8/1994 Adair
5,342,369 A 8/1994 Harryman, II
5,353,974 A 10/1994 Maurizio
5,354,312 A 10/1994 Brinkerhoff et al.
5,364,407 A 11/1994 Poll
5,364,408 A 11/1994 Gordon
5,368,595 A 11/1994 Lewis
5,368,601 A 11/1994 Sauer et al.
5,374,275 A 12/1994 Bradley et al.
5,374,278 A 12/1994 Chesterfield et al.
5,376,096 A 12/1994 Foster
5,383,896 A 1/1995 Gershony et al.
5,383,905 A 1/1995 Golds et al.
5,385,569 A 1/1995 Swor
5,387,221 A 2/1995 Bisgaard
5,387,227 A 2/1995 Grice
5,391,176 A 2/1995 de la Torre
5,391,182 A 2/1995 Chin
5,395,332 A 3/1995 Ressemann et al.
5,395,349 A 3/1995 Quiachon et al.
5,397,310 A 3/1995 Chu et al.
5,397,325 A 3/1995 Della Badia et al.
5,397,326 A 3/1995 Mangum
5,403,329 A 4/1995 Hinchcliffe
5,403,331 A 4/1995 Chesterfield et al.
5,403,338 A 4/1995 Milo
5,405,352 A 4/1995 Weston
5,411,481 A 5/1995 Allen et al.
5,413,571 A 5/1995 Katsaros et al.
5,417,684 A 5/1995 Jackson et al.
5,417,699 A 5/1995 Klein et al.
5,419,765 A 5/1995 Weldon et al.
5,425,705 A 6/1995 Evard et al.
5,425,737 A 6/1995 Burbank et al.
5,425,740 A 6/1995 Hutchinson, Jr.
5,431,666 A 7/1995 Sauer et al.
5,433,700 A 7/1995 Peters
5,452,733 A 9/1995 Sterman et al.
5,454,822 A 10/1995 Schob et al.
5,454,834 A 10/1995 Boebel et al.
5,458,574 A 10/1995 Machold et al.
5,462,560 A 10/1995 Stevens
5,462,561 A 10/1995 Voda
5,464,426 A 11/1995 Bonutti
5,466,241 A 11/1995 Leroy et al.
5,470,338 A 11/1995 Whitfield et al.
5,474,568 A 12/1995 Scott
5,476,469 A 12/1995 Hathaway et al.
5,476,470 A 12/1995 Fitzgibbons, Jr.
5,478,309 A 12/1995 Sweezer et al.
5,478,353 A 12/1995 Yoon
5,480,407 A 1/1996 Wan et al.
5,486,190 A 1/1996 Green
5,489,295 A 2/1996 Piplani et al.
5,496,332 A 3/1996 Sierra et al.
5,507,744 A 4/1996 Tay et al.
5,507,755 A 4/1996 Gresl et al.
5,507,757 A 4/1996 Sauer et al.
5,507,758 A 4/1996 Thomason et al.
5,509,902 A 4/1996 Raulerson
5,520,655 A 5/1996 Davila et al.
5,520,665 A 5/1996 Fleetwood
5,520,691 A 5/1996 Branch
5,520,702 A 5/1996 Sauer et al.
5,527,321 A 6/1996 Hinchliffe
5,527,322 A 6/1996 Klein et al.
D372,310 S 7/1996 Hartnett
5,531,700 A 7/1996 Moore et al.
5,536,273 A 7/1996 Lehrer
5,540,701 A 7/1996 Sharkey et al.
5,540,703 A 7/1996 Barker, Jr. et al.
5,540,704 A 7/1996 Gordon et al.
5,545,171 A 8/1996 Sharkey et al.
5,545,178 A 8/1996 Kensey et al.
5,545,180 A 8/1996 Le et al.
5,549,618 A 8/1996 Fleenor et al.
5,549,631 A 8/1996 Bonutti
5,554,162 A 9/1996 DeLange
5,562,684 A 10/1996 Kammerer
5,562,686 A 10/1996 Sauer et al.
5,562,688 A 10/1996 Riza
5,562,728 A 10/1996 Lazarus et al.
5,567,435 A 10/1996 Hubbell et al.
5,569,269 A 10/1996 Hart et al.
5,569,271 A 10/1996 Hoel
5,571,120 A 11/1996 Yoon
5,573,540 A 11/1996 Yoon
5,584,842 A 12/1996 Fogarty et al.
5,591,177 A 1/1997 Lehrer
5,591,179 A 1/1997 Edelstein
5,591,206 A 1/1997 Moufarrege
5,593,421 A 1/1997 Bauer
5,601,572 A 2/1997 Middleman et al.
5,603,718 A 2/1997 Xu
5,607,435 A 3/1997 Sachdeva et al.
5,609,597 A 3/1997 Lehrer
5,611,794 A 3/1997 Sauer et al.
5,613,974 A 3/1997 Andreas et al.
5,613,975 A 3/1997 Christy
5,624,446 A 4/1997 Harryman, II
5,626,588 A 5/1997 Sauer et al.
5,643,289 A 7/1997 Sauer et al.
5,643,295 A 7/1997 Yoon
5,643,318 A 7/1997 Tsukernik et al.
5,649,959 A 7/1997 Hannam et al.
5,662,664 A 9/1997 Gordon et al.
5,669,917 A 9/1997 Sauer et al.
5,676,689 A 10/1997 Kensey et al.
5,700,273 A 12/1997 Buelna et al.
5,707,379 A 1/1998 Fleenor et al.
5,713,910 A 2/1998 Gordon et al.
5,716,369 A 2/1998 Riza
5,720,574 A 2/1998 Barella
5,720,757 A 2/1998 Hathaway et al.
5,722,981 A 3/1998 Stevens
5,725,552 A 3/1998 Kotula et al.
5,728,109 A 3/1998 Schulze et al.
5,728,114 A 3/1998 Evans et al.
5,728,133 A 3/1998 Kontos
5,728,151 A 3/1998 Garrison et al.
5,741,276 A 4/1998 Poloyko et al.
5,741,280 A 4/1998 Fleenor
5,746,755 A 5/1998 Wood et al.
5,749,890 A 5/1998 Shaknovich
5,755,727 A 5/1998 Kontos
5,759,188 A 6/1998 Yoon
5,766,183 A 6/1998 Sauer
5,766,186 A 6/1998 Faraz et al.
5,766,217 A 6/1998 Christy
5,769,862 A 6/1998 Kammerer et al.
5,779,719 A 7/1998 Klein et al.
5,782,860 A 7/1998 Epstein et al.
5,782,861 A 7/1998 Cragg et al.
5,792,151 A 8/1998 Heck et al.
5,792,152 A 8/1998 Klein et al.
5,797,928 A 8/1998 Kogasaka
5,797,929 A 8/1998 Andreas et al.
5,799,661 A 9/1998 Boyd et al.
5,810,849 A 9/1998 Kontos
5,810,850 A 9/1998 Hathaway et al.
5,814,069 A 9/1998 Schulze et al.
5,817,113 A 10/1998 Gifford, III et al.
5,820,631 A 10/1998 Nobles
5,824,010 A 10/1998 McDonald
5,824,111 A 10/1998 Schall et al.
5,830,125 A 11/1998 Scribner et al.
5,836,955 A 11/1998 Buelna et al.
5,836,956 A 11/1998 Buelna et al.
5,846,253 A 12/1998 Buelna et al.
5,848,714 A 12/1998 Robson et al.
5,855,585 A 1/1999 Kontos

(56) References Cited

U.S. PATENT DOCUMENTS 5,860,963 A 1/1999 Azam et al.
5,860,990 A 1/1999 Nobles et al.
5,860,991 A 1/1999 Klein et al.
5,861,005 A 1/1999 Kontos
5,871,490 A 2/1999 Schulze et al.
5,871,502 A 2/1999 Suryadevara
5,873,876 A 2/1999 Christy
5,876,411 A 3/1999 Kontos
5,897,487 A 4/1999 Ouchi
5,897,564 A 4/1999 Schulze et al.
5,902,311 A 5/1999 Andreas et al.
5,904,597 A 5/1999 Doi et al.
5,904,690 A 5/1999 Middleman et al.
5,904,697 A 5/1999 Gifford, III et al.
5,906,631 A 5/1999 Imran
5,919,207 A 7/1999 Taheri
5,921,994 A 7/1999 Andreas et al.
5,928,266 A 7/1999 Kontos
5,951,590 A 9/1999 Goldfarb
5,954,732 A 9/1999 Hart et al.
5,957,936 A 9/1999 Yoon et al.
5,957,937 A 9/1999 Yoon
5,957,938 A 9/1999 Zhu et al.
5,964,773 A 10/1999 Greenstein
5,964,782 A 10/1999 Lafontaine et al.
5,972,030 A 10/1999 Garrison et al.
5,976,161 A 11/1999 Kirsch et al.
5,980,539 A 11/1999 Kontos
5,997,555 A 12/1999 Kontos
6,001,109 A 12/1999 Kontos
6,022,372 A 2/2000 Kontos
6,024,747 A 2/2000 Kontos
6,036,699 A 3/2000 Andreas et al.
6,042,601 A 3/2000 Smith
6,048,351 A 4/2000 Gordon et al.
6,048,354 A 4/2000 Lawrence
6,048,357 A 4/2000 Kontos
6,068,603 A 5/2000 Suzuki
6,077,276 A 6/2000 Kontos
6,077,279 A 6/2000 Kontos
6,117,144 A 9/2000 Nobles et al.
6,117,145 A 9/2000 Wood et al.
6,126,675 A 10/2000 Shchervinsky et al.
6,132,439 A 10/2000 Kontos
6,132,440 A 10/2000 Hathaway et al.
6,136,010 A 10/2000 Modesitt et al.
6,139,556 A 10/2000 Kontos
6,152,936 A 11/2000 Christy et al.
6,165,183 A 12/2000 Kuehn et al.
6,165,204 A 12/2000 Levinson et al.
6,190,396 B1 2/2001 Whitin et al.
6,197,042 B1 3/2001 Ginn et al.
6,206,893 B1 3/2001 Klein et al.
6,206,895 B1 3/2001 Levinson
6,245,079 B1 6/2001 Nobles et al.
6,248,124 B1 6/2001 Pedros et al.
6,296,657 B1 10/2001 Brucker
6,348,059 B1 2/2002 Hathaway et al.
6,355,050 B1 3/2002 Andreas et al.
6,358,258 B1 3/2002 Arcia et al.
6,395,015 B1 5/2002 Borst et al.
6,428,472 B1 8/2002 Haas
6,428,549 B1 8/2002 Kontos
6,436,109 B1 8/2002 Kontos
6,443,963 B1 9/2002 Baldwin et al.
6,451,031 B1 9/2002 Kontos
6,511,489 B2 1/2003 Field et al.
6,517,553 B2 2/2003 Klein et al.
6,533,812 B2 3/2003 Swanson et al.
6,551,330 B1 4/2003 Bain et al.
6,558,399 B1 5/2003 Isbell et al.
6,562,052 B2 5/2003 Nobles et al.
6,569,185 B2 5/2003 Ungs
6,572,629 B2 6/2003 Kalloo et al.
6,610,072 B1 8/2003 Christy et al.
6,623,509 B2 9/2003 Ginn
6,623,510 B2 9/2003 Carley et al.
6,632,237 B2 10/2003 Ben-David et al.
6,641,592 B1 11/2003 Sauer et al.
6,663,655 B2 12/2003 Ginn et al.
6,676,685 B2 1/2004 Pedros et al.
6,695,867 B2 2/2004 Ginn et al.
6,716,228 B2 4/2004 Tal
6,743,195 B2 6/2004 Zucker
6,743,259 B2 6/2004 Ginn
6,749,621 B2 6/2004 Pantages et al.
6,749,622 B2 6/2004 McGuckin, Jr. et al.
6,837,906 B2 1/2005 Ginn
6,846,319 B2 1/2005 Ginn et al.
6,890,343 B2 5/2005 Ginn et al.
6,896,692 B2 5/2005 Ginn et al.
6,911,034 B2 6/2005 Nobles et al.
6,939,357 B2 9/2005 Navarro et al.
6,964,668 B2 11/2005 Modesitt et al.
6,969,397 B2 11/2005 Ginn
7,001,400 B1 2/2006 Modesitt et al.
7,029,480 B2 4/2006 Klein et al.
7,029,481 B1 4/2006 Burdulis, Jr. et al.
7,048,747 B2 5/2006 Arcia et al.
7,063,710 B2 6/2006 Takamoto et al.
7,083,635 B2 8/2006 Ginn
7,108,710 B2 9/2006 Anderson
7,112,225 B2 9/2006 Ginn
7,160,309 B2 1/2007 Voss
7,179,266 B2 2/2007 Kontos
7,229,458 B2 6/2007 Boecker et al.
7,235,087 B2 6/2007 Modesitt et al.
7,316,704 B2 1/2008 Bagaoisan et al.
7,326,230 B2 2/2008 Ravikumar
7,331,979 B2 2/2008 Khosravi et al.
7,335,220 B2 2/2008 Khosravi et al.
7,361,183 B2 4/2008 Ginn
7,361,185 B2 4/2008 O'Malley et al.
7,377,927 B2 5/2008 Burdulis, Jr. et al.
7,390,328 B2 6/2008 Modesitt
7,393,363 B2 7/2008 Ginn
7,442,198 B2 10/2008 Gellman et al.
7,445,626 B2 11/2008 Songer et al.
7,449,024 B2 11/2008 Stafford
7,462,188 B2 12/2008 McIntosh
7,753,923 B2 7/2010 St. Goar et al.
7,837,696 B2 11/2010 Modesitt et al.
7,842,047 B2 11/2010 Modesitt et al.
7,842,048 B2 11/2010 Ma
7,842,049 B2 11/2010 Voss
7,846,170 B2 12/2010 Modesitt et al.
7,850,701 B2 12/2010 Modesitt
7,883,517 B2 2/2011 Pantages et al.
8,038,688 B2 10/2011 Modesitt et al.
8,048,092 B2 11/2011 Modesitt et al.
8,057,491 B2 11/2011 Modesitt et al.
8,083,754 B2 12/2011 Pantages et al.
8,137,364 B2 3/2012 Zung et al.
8,172,860 B2 5/2012 Zung et al.
8,202,281 B2 6/2012 Voss
8,211,122 B2 7/2012 McIntosh
8,252,008 B2 8/2012 Ma
8,257,368 B2 9/2012 McIntosh
8,267,947 B2 9/2012 Pantages et al.
2001/0046518 A1 11/2001 Sawhney
2002/0045908 A1 4/2002 Nobles et al.
2002/0095164 A1 7/2002 Andreas et al.
2002/0099389 A1 7/2002 Michler et al.
2002/0106409 A1 8/2002 Sawhney et al.
2002/0177876 A1 11/2002 Roby et al.
2003/0093093 A1 5/2003 Modesitt et al.
2003/0195529 A1 10/2003 Takamoto et al.
2004/0009205 A1 1/2004 Sawhney
2004/0092964 A1 5/2004 Modesitt et al.
2004/0093027 A1 5/2004 Fabisiak et al.
2004/0097978 A1 5/2004 Modesitt et al.
2004/0127940 A1 7/2004 Ginn et al.
2004/0143290 A1 7/2004 Brightbill
2004/0158127 A1 8/2004 Okada

(56) References Cited

U.S. PATENT DOCUMENTS

2004/0158287 A1 8/2004 Cragg et al.
2004/0167511 A1 8/2004 Buehlmann et al.
2004/0181238 A1 9/2004 Zarbatany et al.
2004/0186487 A1 9/2004 Klein et al.
2004/0191277 A1 9/2004 Sawhney et al.
2004/0210251 A1 10/2004 Kontos
2004/0215232 A1 10/2004 Belhe et al.
2004/0225301 A1 11/2004 Roop et al.
2004/0267193 A1 12/2004 Bagaoisan et al.
2004/0267308 A1 12/2004 Bagaoisan et al.
2005/0070923 A1 3/2005 McIntosh
2005/0075665 A1 4/2005 Brenzel et al.
2005/0085851 A1 4/2005 Fiehler et al.
2005/0085854 A1 4/2005 Ginn
2005/0085855 A1 4/2005 Forsberg
2005/0121042 A1 6/2005 Belhe et al.
2005/0149117 A1 7/2005 Khosravi et al.
2005/0177189 A1 8/2005 Ginn et al.
2005/0222614 A1 10/2005 Ginn et al.
2005/0245876 A1 11/2005 Khosravi et al.
2005/0267528 A1 12/2005 Ginn et al.
2005/0273137 A1 12/2005 Ginn
2006/0034930 A1 2/2006 Khosravi et al.
2006/0047313 A1 3/2006 Khanna et al.
2006/0100664 A1 5/2006 Pai et al.
2006/0167477 A1 7/2006 Arcia et al.
2006/0173469 A1 8/2006 Klein et al.
2006/0253037 A1 11/2006 Ginn et al.
2006/0253072 A1 11/2006 Pai et al.
2007/0032801 A1 2/2007 Pantages et al.
2007/0060950 A1 3/2007 Khosravi et al.
2007/0123817 A1 5/2007 Khosravi et al.
2007/0282354 A1 12/2007 McIntosh
2008/0009794 A1 1/2008 Bagaoisan et al.
2008/0065151 A1 3/2008 Ginn
2008/0065152 A1 3/2008 Carley
2008/0287967 A1 11/2008 Andreas et al.
2008/0319458 A1 12/2008 Reynolds
2009/0036906 A1 2/2009 Stafford
2009/0048615 A1 2/2009 McIntosh
2009/0088779 A1 4/2009 Zung et al.
2011/0066184 A1 3/2011 Modesitt et al.
2011/0071567 A1 3/2011 Modesitt et al.
2011/0196387 A1 8/2011 Pantages et al.
2012/0053600 A1 3/2012 Fortson
2012/0150201 A1 6/2012 Pantages et al.
2012/0316579 A1 12/2012 Ma
2013/0012962 A1 1/2013 Stone
2013/0066340 A1 3/2013 Pantages et al.

FOREIGN PATENT DOCUMENTS

DE 9217932 7/1993
DE 4220283 12/1993
DE 10211360 10/2003
EP 0 140 557 5/1985
EP 0 207 545 1/1987
EP 0 474 887 3/1992
EP 0 478 358 4/1992
EP 0 478 887 4/1992
EP 0 542 126 5/1993
EP 0 568 098 11/1993
EP 0 589 409 3/1994
EP 0 624 343 11/1994
EP 0 669 101 8/1995
EP 0 669 102 8/1995
EP 0 669 103 8/1995
EP 0 684 012 11/1995
EP 0 812 571 12/1997
EP 0 941 698 9/1999
FR 1059544 3/1954
FR 2768324 3/1999
JP 51143386 11/1976
JP 5220794 2/1977
JP 2119866 5/1990
JP 542161 2/1993
SU 820810 4/1981
SU 993922 2/1983
SU 1093329 5/1984
SU 1174036 8/1985
SU 1544383 2/1990
SU 1648400 5/1991
WO WO 85/03858 9/1985
WO WO 94/05213 3/1994
WO WO 94/13211 6/1994
WO WO 94/27503 12/1994
WO WO 94/28801 12/1994
WO WO 95/05121 2/1995
WO WO 95/13021 5/1995
WO WO 95/25468 9/1995
WO WO 95/35065 12/1995
WO WO 96/09006 3/1996
WO WO 97/00046 1/1997
WO WO 97/03613 2/1997
WO WO 97/07745 3/1997
WO WO 97/10764 3/1997
WO WO 97/13461 4/1997
WO WO 97/17901 5/1997
WO WO 97/20505 6/1997
WO WO 97/27897 8/1997
WO WO 98/04195 2/1998
WO WO 98/42262 10/1998
WO WO 99/47049 9/1999
WO WO 00/12013 3/2000
WO WO 00/51498 9/2000
WO WO 00/69342 11/2000
WO WO 01/19259 3/2001
WO WO 01/35833 5/2001
WO WO 02/36021 5/2002
WO WO 02/062234 8/2002
WO WO 03/003925 1/2003
WO WO 03/094748 11/2003
WO WO 03/099134 12/2003
WO WO 2005/000126 1/2005
WO WO 2005/023119 3/2005
WO WO 2005/025430 3/2005
WO WO 2005/030060 4/2005
WO WO 2005/041782 5/2005
WO WO 2005/063129 7/2005
WO WO 2005/065549 7/2005
WO WO 2005/092204 10/2005
WO WO 2005/112782 12/2005
WO WO 2006/026116 3/2006
WO WO 2006/052611 5/2006
WO WO 2006/052612 5/2006
WO WO 2006/078578 7/2006
WO WO 2006/115901 11/2006
WO WO 2006/115904 11/2006
WO WO 2006/118877 11/2006
WO WO 2007/019016 2/2007
WO WO 2007/081836 7/2007

OTHER PUBLICATIONS

U.S. Appl. No. 13/022,050, mailed Oct. 31, 2012, Issue Notification.
U.S. Appl. No. 10/948,445, filed Sep. 22, 2004, McIntosh.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 13/525,875, filed Jun. 18, 2012, Voss.
U.S. Appl. No. 90/006,469, filed Nov. 29, 2002, Modesitt et al.
Cardiac Catheterization and Angiography, 3rd Ed., Lea & Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.

(56) References Cited

OTHER PUBLICATIONS

Marshall, A.C & Lock, J.E. "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintcchnik GmbH, Product Brochure entitled "REMA," Apr. 2001, 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, mailed May 12, 1993, Office Action.
U.S. Appl. No. 07/989,611, mailed Aug. 1, 1994, Office Action.
U.S. Appl. No. 07/989,611, mailed Nov. 3, 1994, Notice of Allowance.
U.S. Appl. No. 08/148,809, mailed Sep. 16, 1994, Office Action.
U.S. Appl. No. 08/148,809, mailed May 30, 1995, Office Action.
U.S. Appl. No. 08/148,809, mailed Dec. 15, 1995, Notice of Allowance.
U.S. Appl. No. 08/252,124, mailed Jun. 5, 1995, Office Action.
U.S. Appl. No. 08/252,124, mailed Jan. 5, 1996, Office Action.
U.S. Appl. No. 08/252,124, mailed May 22, 1996, Notice of Allowance.
U.S. Appl. No. 08/259,410, mailed Feb. 2, 1995, Office Action.
U.S. Appl. No. 08/259,410, mailed Jun. 1, 1995, Office Action.
U.S. Appl. No. 08/259,410, mailed Feb. 6, 1998, Notice of Allowance.
U.S. Appl. No. 08/638,076, mailed Jan. 21, 1997, Office Action.
U.S. Appl. No. 08/638,076, mailed Oct. 17, 1997, Notice of Allowance.
U.S. Appl. No. 08/824,031, mailed Mar. 16, 1998, Office Action.
U.S. Appl. No. 08/824,031, mailed Sep. 14, 1998, Office Action.
U.S. Appl. No. 08/824,031, mailed Apr. 13, 1999, Office Action.
U.S. Appl. No. 08/824,031, mailed Jul. 15, 1999, Notice of Allowance.
U.S. Appl. No. 08/883,246, mailed Jul. 23, 1998, Office Action.
U.S. Appl. No. 08/883,246, mailed Apr. 12, 1999, Office Action.
U.S. Appl. No. 08/883,246, mailed Oct. 13, 1999, Office Action.
U.S. Appl. No. 08/883,246, mailed Oct. 23, 2000, Office Action.
U.S. Appl. No. 08/883,246, mailed Jul. 11, 2001, Office Action.
U.S. Appl. No. 08/883,246, mailed Sep. 11, 2001, Notice of Allowance.
U.S. Appl. No. 09/057,108, mailed Jul. 10, 2000, Office Action.
U.S. Appl. No. 09/057,108, mailed Oct. 25, 2000, Notice of Allowance.
U.S. Appl. No. 09/262,402, mailed Mar. 29, 2000, Office Action.
U.S. Appl. No. 09/262,402, mailed May 30, 2000, Notice of Allowance.
U.S. Appl. No. 09/395,901, mailed Jun. 27, 2000, Office Action.
U.S. Appl. No. 09/395,901, mailed Nov. 6, 2000, Office Action.
U.S. Appl. No. 09/395,901, mailed Apr. 20, 2001, Notice of Allowance.
U.S. Appl. No. 09/395,901, mailed Sep. 10, 2001, Notice of Allowance.
U.S. Appl. No. 09/610,099, mailed Jul. 11, 2002, Office Action.
U.S. Appl. No. 09/610,099, mailed Dec. 24, 2002, Notice of Allowance.
U.S. Appl. No. 09/651,344, mailed Feb. 28, 2003, Office Action.
U.S. Appl. No. 09/651,344, mailed Nov. 7, 2003, Office Action.
U.S. Appl. No. 09/651,344, mailed Apr. 20, 2004, Notice of Allowance.
U.S. Appl. No. 09/707,746, mailed Feb. 16, 2005, Office Action.
U.S. Appl. No. 09/707,746, mailed Jul. 7, 2005, Office Action.
U.S. Appl. No. 09/707,746, mailed Nov. 15, 2005, Notice of Allowance.
U.S. Appl. No. 09/769,109, mailed Oct. 23, 2001, Office Action.
U.S. Appl. No. 09/769,109, mailed Jun. 17, 2002, Office Action.
U.S. Appl. No. 09/769,109, mailed Sep. 9, 2002, Notice of Allowance.
U.S. Appl. No. 09/988,541, mailed Mar. 17, 2004, Office Action.
U.S. Appl. No. 09/988,541, mailed Feb. 28, 2005, Office Action.
U.S. Appl. No. 09/988,541, mailed May 25, 2005, Office Action.
U.S. Appl. No. 09/988,541, mailed Aug. 24, 2005, Office Action.
U.S. Appl. No. 09/988,541, mailed Nov. 8, 2005, Office Action.
U.S. Appl. No. 09/988,541, mailed Dec. 13, 2005, Notice of Allowance.
U.S. Appl. No. 10/033,689, mailed Sep. 30, 2003, Office Action.
U.S. Appl. No. 10/152,272, mailed Jan. 24, 2005, Office Action.
U.S. Appl. No. 10/152,272, mailed May 13, 2005, Notice of Allowance.
U.S. Appl. No. 10/335,065, mailed Mar. 17, 2005, Office Action.
U.S. Appl. No. 10/335,065, mailed Jun. 10, 2005, Office Action.
U.S. Appl. No. 10/335,065, mailed Nov. 17, 2005, Notice of Allowance.
U.S. Appl. No. 10/335,147, mailed Dec. 13, 2005, Office Action.
U.S. Appl. No. 10/335,147, mailed Apr. 17, 2006, Office Action.
U.S. Appl. No. 10/335,147, mailed Oct. 4, 2006, Notice of Allowance.
U.S. Appl. No. 10/357,984, mailed Jan. 9, 2006, Office Action.
U.S. Appl. No. 10/357,984, mailed Mar. 16, 2006, Office Action.
U.S. Appl. No. 10/357,984, mailed Sep. 28, 2006, Office Action.
U.S. Appl. No. 10/357,984, mailed Mar. 23, 2007, Office Action.
U.S. Appl. No. 10/357,984, mailed Nov. 14, 2007, Office Action.
U.S. Appl. No. 10/652,182, mailed Aug. 9, 2006, Office Action.
U.S. Appl. No. 10/652,182, Feb. 22, 2007, Notice of Allowance.
U.S. Appl. No. 10/660,288, mailed Nov. 15, 2005, Office Action.
U.S. Appl. No. 10/660,288, mailed Mar. 9, 2006, Office Action.
U.S. Appl. No. 10/660,288, mailed Aug. 24, 2006, Office Action.
U.S. Appl. No. 10/660,288, mailed Feb. 1, 2007, Office Action.
U.S. Appl. No. 10/660,288, mailed Jun. 28, 2007, Office Action.
U.S. Appl. No. 10/660,288, mailed Apr. 29, 2009, Office Action.
U.S. Appl. No. 10/660,288, mailed Aug. 3, 2009, Office Action.
U.S. Appl. No. 10/660,288, mailed Mar. 30, 2010, Office Action.
U.S. Appl. No. 10/660,288, mailed Mar. 29, 2011, Office Action.
U.S. Appl. No. 10/660,288, mailed Sep. 30, 2011, Notice of Allowance.
U.S. Appl. No. 10/729,541, mailed Dec. 12, 2006, Office Action.
U.S. Appl. No. 10/729,541, mailed Jun. 18, 2007, Office Action.
U.S. Appl. No. 10/729,541, mailed Jan. 8, 2008, Office Action.
U.S. Appl. No. 10/729,541, mailed Sep. 23, 2008, Office Action.
U.S. Appl. No. 10/729,541, mailed May 1, 2009, Office Action.
U.S. Appl. No. 10/729,541, mailed Nov. 16, 2009, Notice of Allowance.
U.S. Appl. No. 10/729,541, mailed Mar. 25, 2010, Notice of Allowance.
U.S. Appl. No. 10/729,541, mailed Jul. 12, 2010, Notice of Allowance.
U.S. Appl. No. 10/729,541, mailed Nov. 3, 2010, Issue Notification.
U.S. Appl. No. 10/737,668, mailed Nov. 2, 2005, Office Action.
U.S. Appl. No. 10/737,668, mailed Feb. 16, 2006, Office Action.
U.S. Appl. No. 10/737,668, mailed Oct. 19, 2006, Office Action.
U.S. Appl. No. 10/737,668, mailed Jun. 7, 2007, Office Action.
U.S. Appl. No. 10/737,668, mailed Nov. 28, 2007, Office Action.
U.S. Appl. No. 10/737,668, mailed Jun. 26, 2008, Notice of Allowance.
U.S. Appl. No. 10/742,406, mailed Mar. 23, 2007, Office Action.
U.S. Appl. No. 10/742,406, mailed Sep. 10, 2007, Notice of Allowance.
U.S. Appl. No. 10/742,406, mailed Jan. 11, 2008, Notice of Allowance.
U.S. Appl. No. 10/746,210, mailed Apr. 5, 2007, Office Action.
U.S. Appl. No. 10/746,210, mailed Aug. 21, 2007, Office Action.
U.S. Appl. No. 10/746,210, mailed Jul. 9, 2008, Notice of Allowance.
U.S. Appl. No. 10/813,449, mailed Sep. 5, 2006, Office Action.
U.S. Appl. No. 10/813,449, mailed Jul. 16, 2007, Office Action.
U.S. Appl. No. 10/813,449, mailed Jan. 25, 2008, Office Action.

(56) References Cited

OTHER PUBLICATIONS

U.S. Appl. No. 10/813,449, mailed Aug. 14, 2008, Office Action.
U.S. Appl. No. 10/813,449, mailed Sep. 15, 2008, Office Action.
U.S. Appl. No. 10/813,449, mailed Feb. 3, 2009, Office Action.
U.S. Appl. No. 10/813,449, mailed Aug. 28, 2009, Office Action.
U.S. Appl. No. 10/813,449, mailed May 27, 2010, Office Action.
U.S. Appl. No. 10/909,531, mailed Apr. 4, 2007, Office Action.
U.S. Appl. No. 10/909,531, mailed Dec. 26, 2007, Office Action.
U.S. Appl. No. 10/909,531, mailed Jun. 13, 2008, Office Action.
U.S. Appl. No. 10/909,531, mailed Feb. 9, 2009, Office Action.
U.S. Appl. No. 10/909,531, mailed Sep. 16, 2009, Office Action.
U.S. Appl. No. 10/909,531, mailed Apr. 29, 2010, Notice of Allowance.
U.S. Appl. No. 10/909,531, mailed Aug. 20, 2010, Notice of Allowance.
U.S. Appl. No. 10/909,531, mailed Nov. 23, 2010, Issue Notification.
U.S. Appl. No. 10/948,445, mailed Jul. 11, 2007, Office Action.
U.S. Appl. No. 11/199,338, mailed Jan. 25, 2007, Office Action.
U.S. Appl. No. 11/199,338, mailed Oct. 5, 2007, Office Action.
U.S. Appl. No. 11/199,338, mailed Dec. 28, 2007, Office Action.
U.S. Appl. No. 11/199,338, mailed Apr. 23, 2008, Office Action.
U.S. Appl. No. 11/199,338, mailed Jan. 6, 2009, Office Action.
U.S. Appl. No. 11/199,496, mailed Apr. 1, 2009, Office Action.
U.S. Appl. No. 11/199,496, mailed Aug. 21, 2009, Office Action.
U.S. Appl. No. 11/199,496, mailed Apr. 23, 2010, Office Action.
U.S. Appl. No. 11/199,496, mailed Apr. 28, 2011, Office Action.
U.S. Appl. No. 11/199,496, mailed Aug. 18, 2011, Notice of Allowance.
U.S. Appl. No. 11/199,515, mailed Aug. 20, 2008, Office Action.
U.S. Appl. No. 11/199,515, mailed Nov. 13, 2008, Office Action.
U.S. Appl. No. 11/199,515, mailed Jun. 10, 2009, Office Action.
U.S. Appl. No. 11/199,515, mailed Dec. 24, 2009, Notice of Allowance.
U.S. Appl. No. 11/199,515, mailed Apr. 2, 2010, Notice of Allowance.
U.S. Appl. No. 11/199,515, mailed Aug. 2, 2010, Notice of Allowance.
U.S. Appl. No. 11/273,107, mailed Jun. 14, 2007, Office Action.
U.S. Appl. No. 11/273,107, mailed Jan. 18, 2008, Office Action.
U.S. Appl. No. 11/273,107, mailed Sep. 5, 2008, Office Action.
U.S. Appl. No. 11/273,107, mailed Apr. 9, 2009, Office Action.
U.S. Appl. No. 11/273,107, mailed Oct. 28, 2009, Office Action.
U.S. Appl. No. 11/273,107, mailed Jun. 2, 2010, Office Action.
U.S. Appl. No. 11/273,107, mailed Oct. 27, 2010, Office Action.
U.S. Appl. No. 11/273,107, mailed Jun. 2, 2011, Notice of Allowance.
U.S. Appl. No. 11/363,005, mailed Jun. 22, 2007, Office Action.
U.S. Appl. No. 11/363,005, mailed Dec. 14, 2007, Office Action.
U.S. Appl. No. 11/363,005, mailed Apr. 17, 2008, Office Action.
U.S. Appl. No. 11/363,005, mailed Dec. 23, 2008, Office Action.
U.S. Appl. No. 11/363,005, mailed Jul. 10, 2009, Notice of Allowance.
U.S. Appl. No. 11/363,005, mailed Jan. 14, 2010, Notice of Allowance.
U.S. Appl. No. 11/363,005, mailed Jul. 23, 2010, Notice of Allowance.
U.S. Appl. No. 11/363,005, mailed Nov. 10, 2010, Issue Notification.
U.S. Appl. No. 11/389,762, mailed Sep. 20, 2007, Notice of Allowance.
U.S. Appl. No. 11/389,762, mailed Nov. 23, 2007, Notice of Allowance.
U.S. Appl. No. 11/390,937, mailed Sep. 7, 2007, Office Action.
U.S. Appl. No. 11/391,951, mailed Oct. 28, 2008, Office Action.
U.S. Appl. No. 11/391,951, mailed Jan. 30, 2009, Office Action.
U.S. Appl. No. 11/391,951, mailed Aug. 26, 2009, Office Action.
U.S. Appl. No. 11/391,951, mailed Jun. 23, 2010, Office Action.
U.S. Appl. No. 11/465,527, mailed Feb. 3, 2010, Office Action.
U.S. Appl. No. 11/465,527, mailed Jul. 23, 2010, Notice of Allowance.
U.S. Appl. No. 11/465,527, mailed Nov. 10, 2010, Issue Notification.
U.S. Appl. No. 11/552,593, mailed Aug. 21, 2008, Office Action.
U.S. Appl. No. 11/552,593, mailed Feb. 5, 2009, Office Action.
U.S. Appl. No. 11/552,593, mailed Oct. 13, 2009, Notice of Allowance.
U.S. Appl. No. 11/552,593, mailed Mar. 22, 2010, Notice of Allowance.
U.S. Appl. No. 11/552,593, mailed Jul. 22, 2010, Notice of Allowance.
U.S. Appl. No. 11/552,593, mailed Nov. 10, 2010, Issue Notification.
U.S. Appl. No. 11/688,722, mailed Mar. 10, 2010, Office Action.
U.S. Appl. No. 11/688,722, mailed Jul. 29, 2010, Notice of Allowance.
U.S. Appl. No. 11/688,722, mailed Nov. 17, 2010, Issue Notification.
U.S. Appl. No. 11/891,358, mailed Apr. 26, 2010, Office Action.
U.S. Appl. No. 11/891,358, mailed Oct. 19, 2010, Office Action.
U.S. Appl. No. 11/891,358, mailed Aug. 31, 2011, Office Action.
U.S. Appl. No. 11/891,358, mailed Nov. 18, 2011, Notice of Allowance.
U.S. Appl. No. 11/891,358, mailed Apr. 10, 2012, Notice of Allowance.
U.S. Appl. No. 11/891,513, mailed Apr. 9, 2010, Office Action.
U.S. Appl. No. 11/891,513, mailed Sep. 28, 2010, Office Action.
U.S. Appl. No. 11/891,513, mailed Aug. 31, 2011, Office Action.
U.S. Appl. No. 11/891,513, mailed Nov. 1, 2011, Notice of Allowance.
U.S. Appl. No. 11/891,513, mailed May 8, 2012, Notice of Allowance.
U.S. Appl. No. 11/960,593, mailed Sep. 14, 2010, Office Action.
U.S. Appl. No. 11/960,593, mailed Nov. 3, 2010, Office Action.
U.S. Appl. No. 11/960,593, mailed Apr. 28, 2011, Office Action.
U.S. Appl. No. 11/997,379, mailed Jul. 13, 2011, Office Action.
U.S. Appl. No. 11/997,379, mailed Feb. 28, 2012, Office Action.
U.S. Appl. No. 11/997,379, mailed May 11, 2012, Notice of Allowance.
U.S. Appl. No. 12/182,836, mailed Oct. 5, 2010, Office Action.
U.S. Appl. No. 12/182,836, mailed Jun. 23, 2011, Office Action.
U.S. Appl. No. 12/247,012, mailed Oct. 13, 2011, Office Action.
U.S. Appl. No. 12/247,012, mailed Mar. 16, 2012, Office Action.
U.S. Appl. No. 12/247,012, mailed Aug. 13, 2012, Notice of Allowance.
U.S. Appl. No. 12/257,127, mailed Aug. 30, 2010, Office Action.
U.S. Appl. No. 12/257,127, mailed Dec. 22, 2010, Office Action.
U.S. Appl. No. 12/257,127, mailed Jul. 6, 2011, Office Action.
U.S. Appl. No. 12/257,127, mailed Jan. 12, 2012, Office Action.
U.S. Appl. No. 12/334,077, mailed Oct. 27, 2010, Office Action.
U.S. Appl. No. 12/334,077, mailed Jul. 21, 2011, Office Action.
U.S. Appl. No. 12/334,085, mailed Dec. 23, 2010, Office Action.
U.S. Appl. No. 12/334,085, mailed Aug. 4, 2011, Office Action.
U.S. Appl. No. 12/334,085, mailed Jan. 9, 2012, Notice of Allowance.
U.S. Appl. No. 12/873,728, mailed Sep. 11, 2012, Office Action.
U.S. Appl. No. 12/950,338, mailed Jun. 15, 2011, Office Action.
U.S. Appl. No. 12/950,338, mailed Nov. 1, 2011, Notice of Allowance.
U.S. Appl. No. 12/950,338, mailed Aug. 8, 2012, Notice of Allowance.
U.S. Appl. No. 12/955,848, mailed Jun. 30, 2011, Office Action.
U.S. Appl. No. 12/955,848, mailed Nov. 15, 2011, Office Action.
U.S. Appl. No. 12/955,863, mailed Jan. 6, 2012, Office Action.
U.S. Appl. No. 12/955,863, mailed May 15, 2012, Notice of Allowance.
U.S. Appl. No. 12/955,869, mailed Oct. 18, 2011, Office Action.
U.S. Appl. No. 12/955,869, mailed Mar. 22, 2012, Notice of Allowance.
U.S. Appl. No. 12/961,239, mailed Jul. 26, 2011, Notice of Allowance.
U.S. Appl. No. 12/966,961, mailed Aug. 18, 2011, Notice of Allowance.
U.S. Appl. No. 13/022,050, mailed Jul. 11, 2011, Office Action.
U.S. Appl. No. 13/022,050, mailed Apr. 26, 2012, Office Action.
U.S. Appl. No. 13/022,050, mailed Jul. 6, 2012, Notice of Allowance.
U.S. Appl. No. 90/006,469, mailed Nov. 29, 2002, Request for Re-Examination.

(56) References Cited

OTHER PUBLICATIONS

U.S. Appl. No. 90/006,469, mailed Sep. 10, 2004, Office Action.
U.S. Appl. No. 90/006,469, mailed Sep. 27, 2005, Notice of Re-Issue.
U.S. Appl. No. 90/006,469, mailed Jun. 27, 2006, Re-Examination Certification.
U.S. Appl. No. 13/443,659, filed Apr. 10, 2012, Fortson et al.
U.S. Appl. No. 13/445,053, filed Apr. 24, 2012, Fortson et al.
U.S. Appl. No. 12/257,127, mailed Sep. 20, 2012, Notice of Allowance.
U.S. Appl. No. 12/257,127, mailed Jan. 9, 2013, Issue Notification.
U.S. Appl. No. 13/593,154, mailed Jan. 8, 2013, Notice of Allowance.
U.S. Appl. No. 13/752,095, filed Jan. 28, 2013, McIntosh.
U.S. Appl. No. 12/247,012, mailed Mar. 27, 2013, Issue Notification.
U.S. Appl. No. 12/334,077, mailed Jan. 16, 2013, Office Action.
U.S. Appl. No. 13/593,154, mailed Apr. 10, 2013, Issue Notification.
U.S. Appl. No. 12/182,836, mailed Mar. 17, 2013, Office Action.
U.S. Appl. No. 13/870,628, filed Apr. 25, 2013, Ma.
U.S. Appl. No. 12/873,728, mailed May 3, 2013, Office Action.
U.S. Appl. No. 11/960,593, mailed Jul. 1, 2013, Notice of Allowance.

SUTURING DEVICE WITH SPLIT ARM AND METHOD OF SUTURING TISSUE

CROSS-REFERENCE TO RELATED APPLICATIONS

This application is a continuation of U.S. patent application Ser. No. 12/247,012, now U.S. Pat. No. 8,419,753, filed Oct. 7, 2008, which is a Divisional Application of U.S. patent application Ser. No. 10/746,210, filed Dec. 23, 2003, now U.S. Pat. No. 7,449,024 the disclosure of which is incorporated herein by this reference.

BACKGROUND

1. Background and Relevant Art

The present invention relates generally to apparatus and methods for the suturing of body lumens. More particularly, the present invention relates to techniques for percutaneous closure of arterial and venous puncture sites, which are usually accessed through a tissue tract.

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," 3.sup.rd Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudoaneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the arterial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 12, 1996, the full disclosures of which are incorporated herein by reference. A suture-applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device, which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. The new device should have the capability of delivering a pre-tied knot to an incision site. It would be particularly beneficial if these improved devices provided some or all of the benefits while overcoming one or more of the disadvantages discussed above.

2. Description of the Background Art

U.S. Pat. Nos. 5,700,273, 5,836,956, and 5,846,253 describe a wound closure apparatus and method in which needles are threaded with suture inside a blood vessel. U.S. Pat. No. 5,496,332 describes a wound closure apparatus and method for its use, while U.S. Pat. No. 5,364,408 describes an endoscopic suture system.

U.S. Pat. No. 5,374,275 describes a surgical suturing device and method of use, while U.S. Pat. No. 5,417,699 describes a device and method for the percutaneous suturing of a vascular puncture site. An instrument for closing trocar puncture wounds is described in U.S. Pat. No. 5,470,338, and a related device is described in U.S. Pat. No. 5,527,321. U.S. Pat. No. 5,507,757 also describes a method of closing puncture wounds.

U.S. Pat. No. 6,245,079, describes another suturing system, the complete disclosure of which is incorporated herein by reference in its entirety for all purposes.

BRIEF SUMMARY

The present invention provides a device for suturing an opening in a tissue. In various embodiments, the device includes an elongated shaft with a pair of deployable arms. When deployed, these arms are non-perpendicular to the longitudinal axis of the shaft. In one embodiment, the arms are independently deployable. In one embodiment, a first arm is an anterior arm which is deployed by being rotated less than 90 degrees to the longitudinal axis of the shaft, and the second arm is a posterior arm which is deployed by being rotated more than 90 degrees to the longitudinal axis of the shaft. A pivot stop may be provided on the elongated shaft to limit rotation of the arms when they reach their fully deployed position. Each of the first and second arms may include a needle receiving portion thereon. Needles may be advanced longitudinally along the shaft toward the needle receiving portions on the arms. The needles may exit through a side wall of the shaft at a location proximal to the arms.

BRIEF DESCRIPTION OF THE DRAWINGS

(FIG. 1 corresponds to FIG. 41 of U.S. Pat. No. 6,245,079).

(FIG. 2 corresponds to FIG. 42 of U.S. Pat. No. 6,245,079).

(FIG. 3 corresponds to FIG. 47 of U.S. Pat. No. 6,245,079).

DETAILED DESCRIPTION

Figure 1:
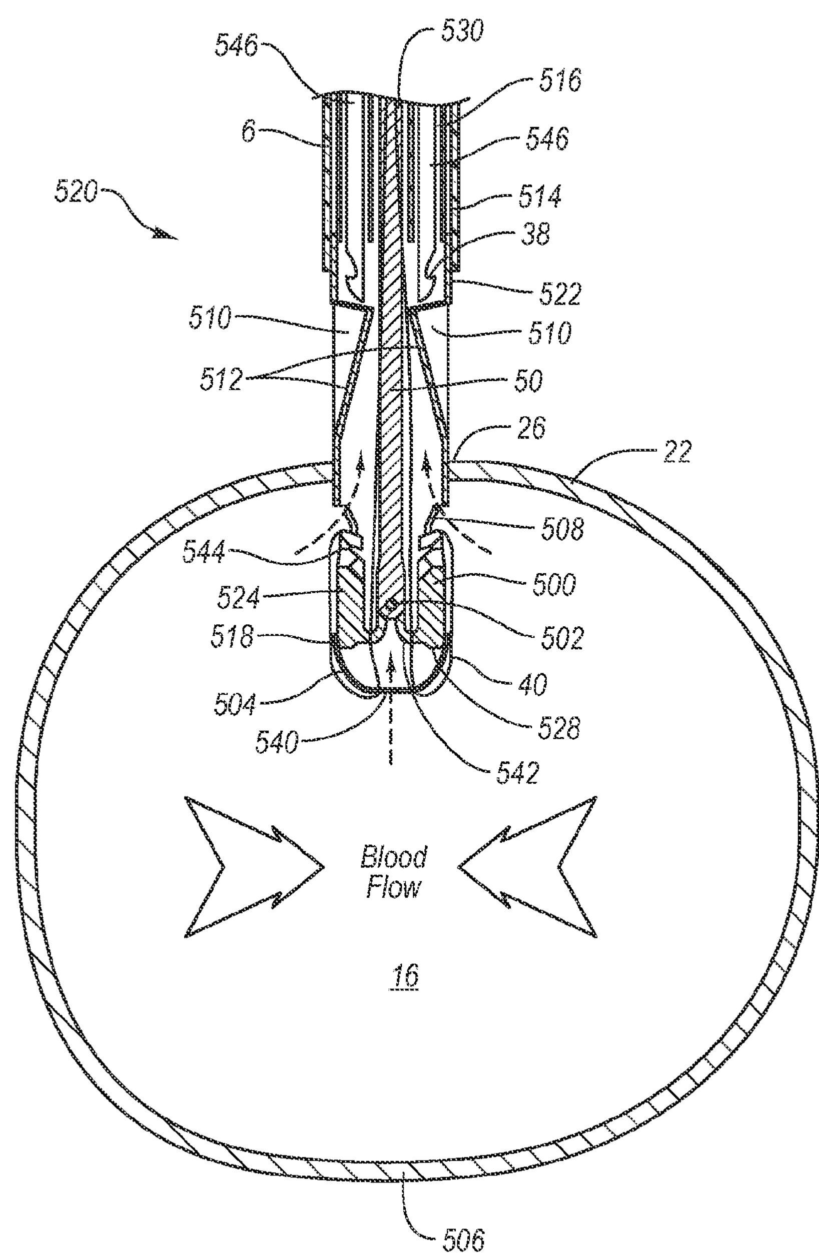
FIG. 1 is a cross-sectional view of a suturing system with its distal end inserted through an arterial wall.
Figure 2:
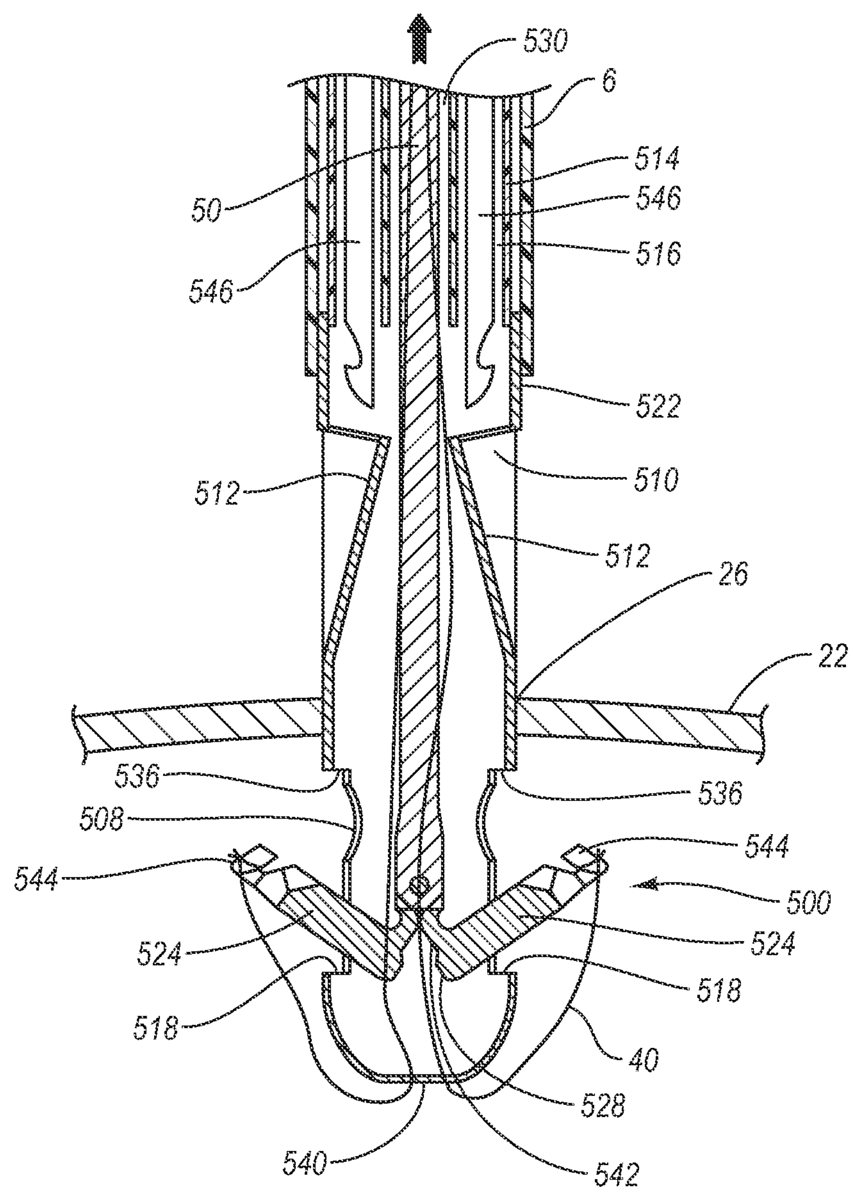
FIG. 2 is a cross-sectional view of the device of FIG. 41 in a partially deployed state.
Figure 3:
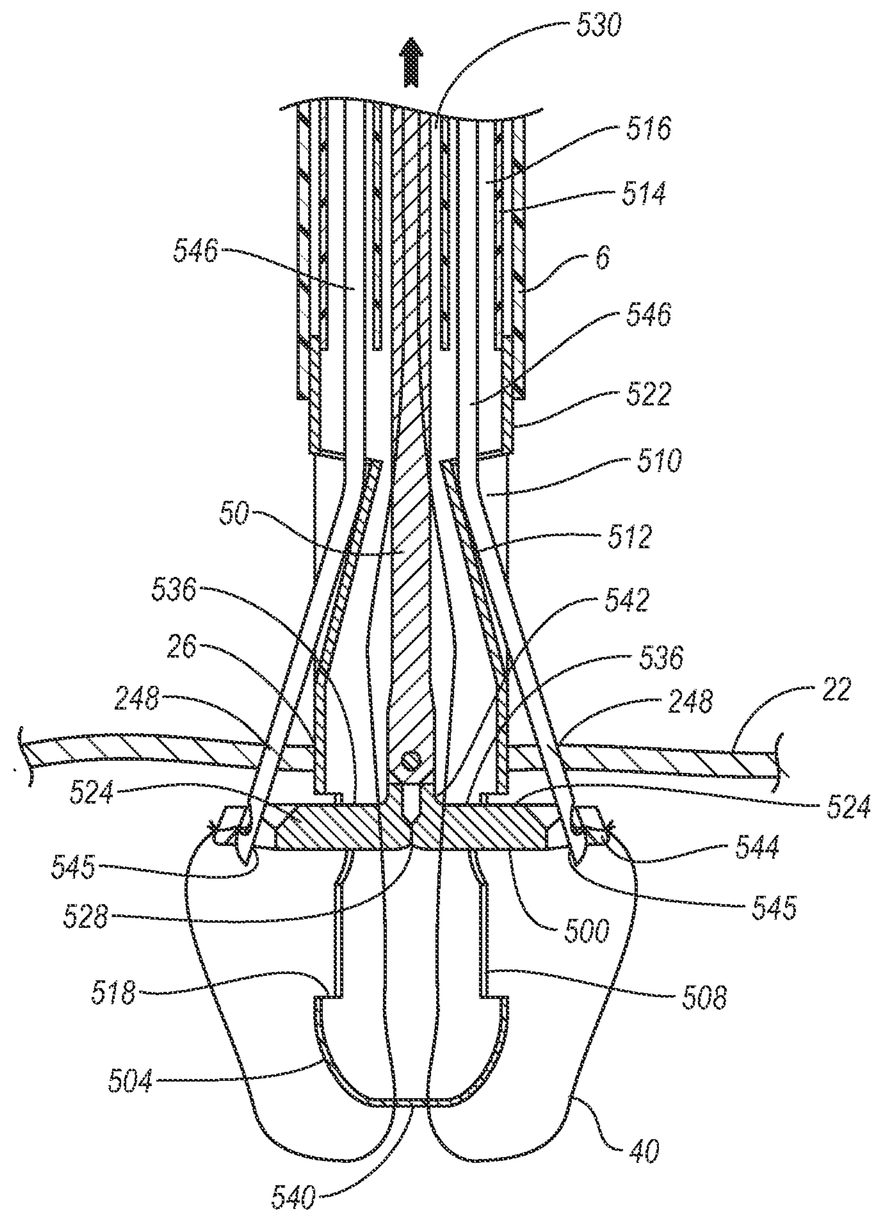
FIG. 3 is cross-sectional view of the device of FIG. 1 with the suture clasp member fully deployed.

FIGS. 1, 2 and 3 show a suturing device corresponding to the suturing device described in U.S. Pat. No. 6,245,079, the complete disclosure of which is incorporated herein by reference in its entirety for all purposes. Specifically, FIGS. 1, 2, and 3 correspond to FIGS. 41, 42 and 47 of U.S. Pat. No. 6,245,079.

Referring to FIG. 1, distal portion of the suturing device 520 is positioned in femoral artery 16. Suturing device 520 comprises a suture introducer head 522 attached to the distal end of a hollow elongated body 514. Suture clasp member 500 and the needles 546 reside in the same longitudinal space. In other words, the needles 546 share the same housing as the suture clasp member 500 (while they are all in their retracted state), but are higher up (proximally) in the suturing device 520 than the suture clasp member 500. Flexible needles 546 bend outward, away from the axis of the device 520, when in the extended position (as shown in FIG. 3).

As shown in FIGS. 2 and 3, the suture introducer head 522 has two needle ports or apertures 510 formed therein (one per needle 546) proximal to the suture clasp arms 524. Each needle port includes a needle guiding portion 512 ("needle guide"), in the form of an outwardly curved groove or channel, which guides the corresponding needle 546 along a particular path. The needle guides 512 may be formed within the suture introducer head 522 (as shown in FIG. 1) as part of a mold, or may be separate pieces (not shown) that are inserted into the suture introducer head 522 during manufacture.

Bleed back is accomplished by the hole 540 at the distal end 504 of the suture introducer head 522, the suture clasp arm apertures 508 and any other openings in the suture introducer head 522. The direction of blood flow for bleed back is shown by the dashed arrows in FIG. 1.

Suture 40 closes the artery vessel opening 26 transverse to the flow of blood. Proper insertion of the needles 546 reduces the risk of damage to the vessel walls 22, 506.

Suturing device 520 includes a single, resilient suture clasp member 500 attached to the actuating rod 50. The suture clasp member 500 comprises a center or hinge portion 542 and two suture clasp arms 524 (one for each needle 546). Each suture clasp arm 524 has a suture clasp 544 at the end thereof.

The hinge portion 542 of the suture clasp member 500 acts as a "living hinge" because it has a memory which causes the member 500 to return to a partially open, unretracted position (FIG. 2) when a force (applied via rod 50) is released. This can be seen in FIGS. 1 and 2. In FIG. 2, the suture clasp member 500 is deployed in the artery 16 in its predisposed (relaxed or natural) position. In FIG. 1, the suture clasp member 500 is retracted into the suture introducer head 522 in its compressed (stressed or tensed) position. The arms 524 are moved to the retracted position by applying a distal force to the actuator rod 50, which causes the arms to contact deflection surfaces 518 (FIG. 2).

This suture clasp member 500 is preferably composed of a resilient shape memory material such as NITENOL, but may alternatively be composed of another material with spring-like characteristics, such as plastic, spring steel, stainless steel or any variations thereof. Further, the suture clasp member 500 could be composed of two arms that are hingedly connected to the actuating rod 50 without the use of a resilient hinge.

Needles 546 are flexible and preferably made from a material with shape memory, such as SUPERFLEX NITENOL. Alternatively, the needles 546 may be composed of spring steel, surgical stainless steel or any variation thereof.

When the needles 546 are advanced distally and come in contact with the needle insertion guides 512, the needle insertion guides cause the needles 546 to bend radially outward. The needles 546 also preferably further bend slightly (radially outward) when they come in contact with the angled surfaces 545 of the suture clasp arms 524, as shown in FIG. 3. When the needles 546 are retracted into the needle lumens 516, they resume a straight configuration as a result of their resiliency.

The proximal portion of the suturing device 520 preferably includes a handle which allows the physician to externally operate the suture clasp arms 524 and the needles 546 inside the blood vessel 16. This handle preferably has three actions: a first action in which the actuating rod 50 applies a proximal force to the hinge portion 542 to deploy and maintain arms 524 in a fully outward position (FIG. 3); a second action to advance the needles 546 distally (FIG. 3) and pull the needles 546 back proximally using one or more springs; and a third action in which the actuating rod 50 applies a distal force to the hinge portion 542 to retract the arms 524 (FIG. 1).

The locked position of the suture clasp arms 524 provides a stable base or foundation for holding the looped ends of the suture 40 while the needles 546 come in contact with the suture clasp arms 524 and capture the suture 40. The suture clasp arms 524 are locked in the locked position by the proximal force of the actuating rod 50, the stationary inside edges 536 of the apertures 508 and the protrusions 528 at the 'elbow' end of each arm 524 (FIG. 3). Specifically, when the suture clasp arms 524 become substantially parallel with each other (i.e., each arm 524 is at an angle of approximately 90 degrees from the actuating rod 50), the protrusions 528 at the 'elbow' end of each arm 524 come into contact with each other and prevent the arms 524 from bending any further than the configuration shown in FIG. 3. The suture clasp member 500 cannot open any farther, even when the needles 546 are inserted distally and come in contact with the suture clasp arms 524. The protrusions 528 prevent the suture clasp member 500 from moving unintentionally (opening any farther) when the needles 546 come in contact with the suture clasp arms 524. This reduces the risk of the looped ends of the suture 40 being accidentally displaced from the suture clasps 544 when the needles 546 engage the suture clasps 544. Thus, the combination of forces asserted by the actuating rod 50, the proximal inside edges 536 of the aperture 508 and the two protrusions 528 sustain the suture clasp arms 524 in a rigid, locked position to facilitate the proper removal of the suture looped ends from the suture clasps 544.

The slits of the suture clasps 544 are angled in a proximal, radially inward direction. Thus, the face of the looped ends of the suture 40 face in a proximal, radially inward direction. In this configuration, there is less chance of the looped ends of the suture 40 falling off the suture clasps 544 improperly or prematurely. When the needles 546 engage the suture clasp arms 524, the only direction the looped ends may move is in a proximal, radially inward direction, which is in the opposite direction of the inserted needles 546. When the needles 546 retract proximally (as shown in FIG. 3), the looped ends reliably fall into the suture catches 38 of the needles 546. It is the proximal movement of the needles 546 which causes the suture catches 38 on the needles 546 to catch the looped ends of the suture 40. This configuration does not rely on a radially outward tension in the looped ends to fasten the looped ends onto the suture catches 38 when the needles 546 are inserted distally.

The description of each of introducer sheath 6, suture catches 38, needle incisions 248, pivot pin 502 and lumen 530 is provided by reference to identically numbered elements in U.S. Pat. No. 6,245,079.

A first important disadvantage of the suturing system illustrated in FIGS. 1, 2 and 3 is that both of the arms 524 deploy to a position that is exactly 90 degrees from the axis of suturing device. This is because protrusions 528 abut one another when suture clasp 500 is fully opened (as shown in FIG. 3). As described above, and in U.S. Pat. No. 6,245,079, it is an advantage of the system of FIGS. 1 to 3 that arms 542 of suture clasp 500 do not open more than 90 degrees to reduce the risk of the looped ends of the suture 40 being accidentally displaced from the suture clasps 544 when the needles 546 engage the suture clasps 544.

Unfortunately, this is particularly problematic when suturing inside a blood vessel, since it may be preferred to enter the blood vessel at a non-perpendicular (e.g.: oblique) angle. In the system of FIGS. 1 to 3, the distal end of the suturing device must therefore be extended to some distance into the blood vessel during operation.

A first feature of the embodiments of the present split arm suturing device is that each of its arms may be extended to different angles from the body of the device. In various embodiments, such angles are non-perpendicular to the longitudinal axis of the suturing device. More particularly, one arm may be extended to a position less than 90 degrees to the body of the device, whereas the other arm may be extended to a position more than 90 degrees to the body of the device.

A second feature of various embodiments of the present split arm suturing device is that each of its arms may be extended one at a time.

Separately, or taken together, these two features of the present invention provide a system which may be conveniently positioned to enter the blood vessel at a non-perpendicular angle, thus minimizing the potential for damage to the blood vessel, while ensuring proper placement of the suture. Thus, an operator can gain better access to smaller arteries and maintain a smaller elbow height, as compared to the suturing device of FIGS. 1 to 3. Thus, the present independently operable split arm suturing device offers significantly increased flexibility to the operator, as compared to the suturing device of FIGS. 1 to 3.

Figure 4A:
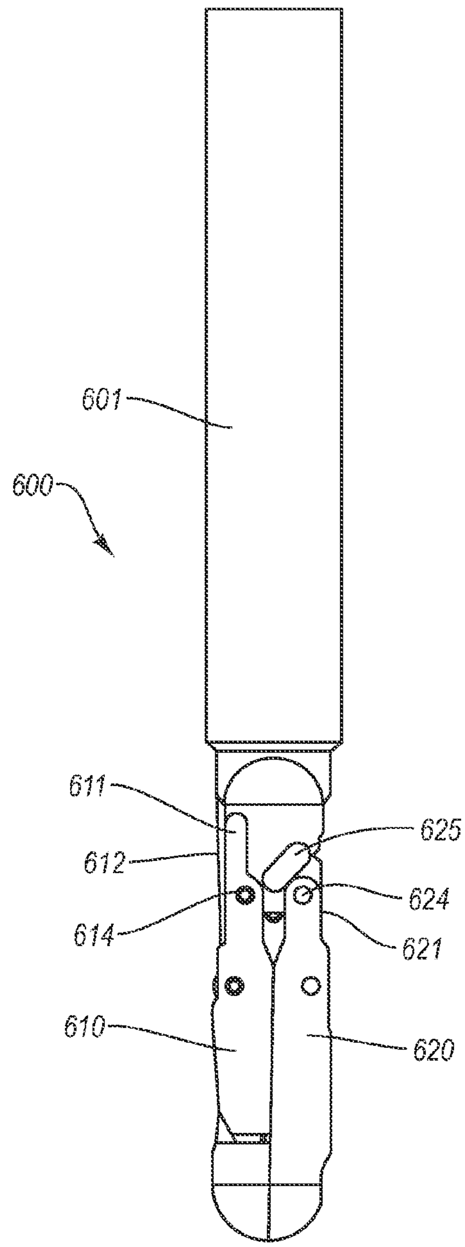
FIG. 4A is a front plan view of the present invention in its compact position (i.e. prior to deployment).
Figure 4B:
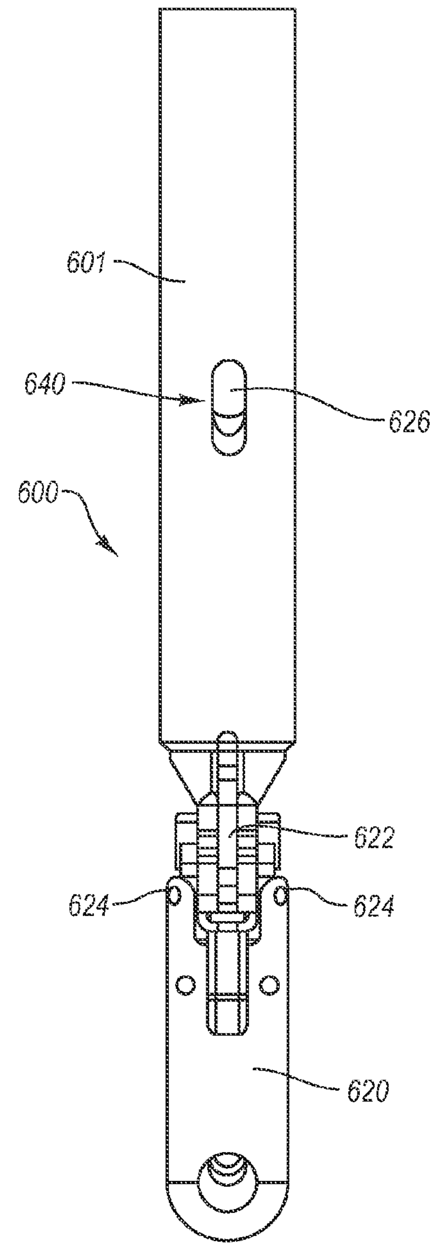
FIG. 4B is a left side elevation view of the present invention prior to deployment.

Referring first to FIGS. 4A and 4B, split arm suturing device 600 is shown prior to deployment (i.e. in its compact position). Suturing device 600 has moveable arms 610 and 620 which can be pivoted relative to the longitudinal axis L of suturing device 600. Arms 610 and 620 may be independently moveable. As will be shown herein, when deployed, arm 610 will preferably be deployed in an anterior direction, and arm 620 will preferably be deployed in a posterior direction.

Figure 5A:
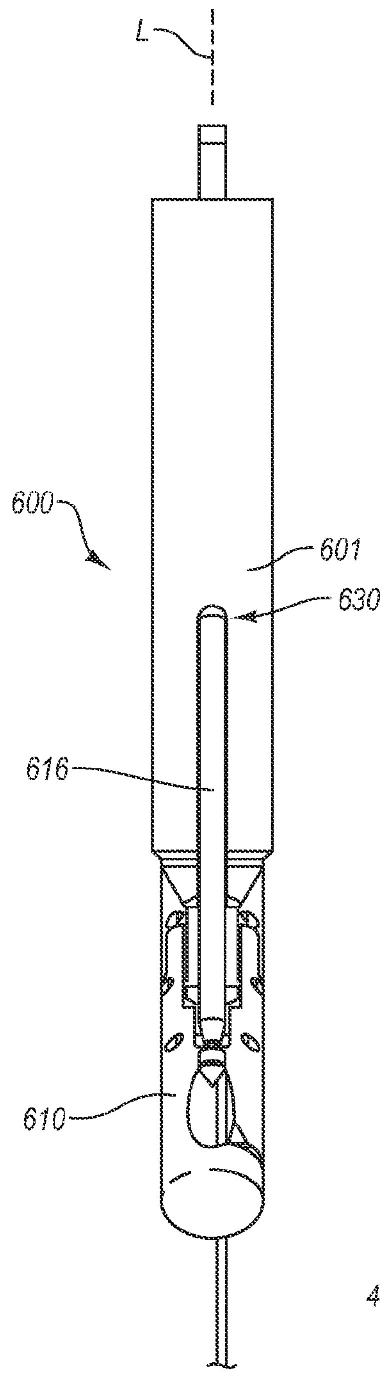
FIG. 5A is a front plan view of the present invention after deployment.
Figure 5B:
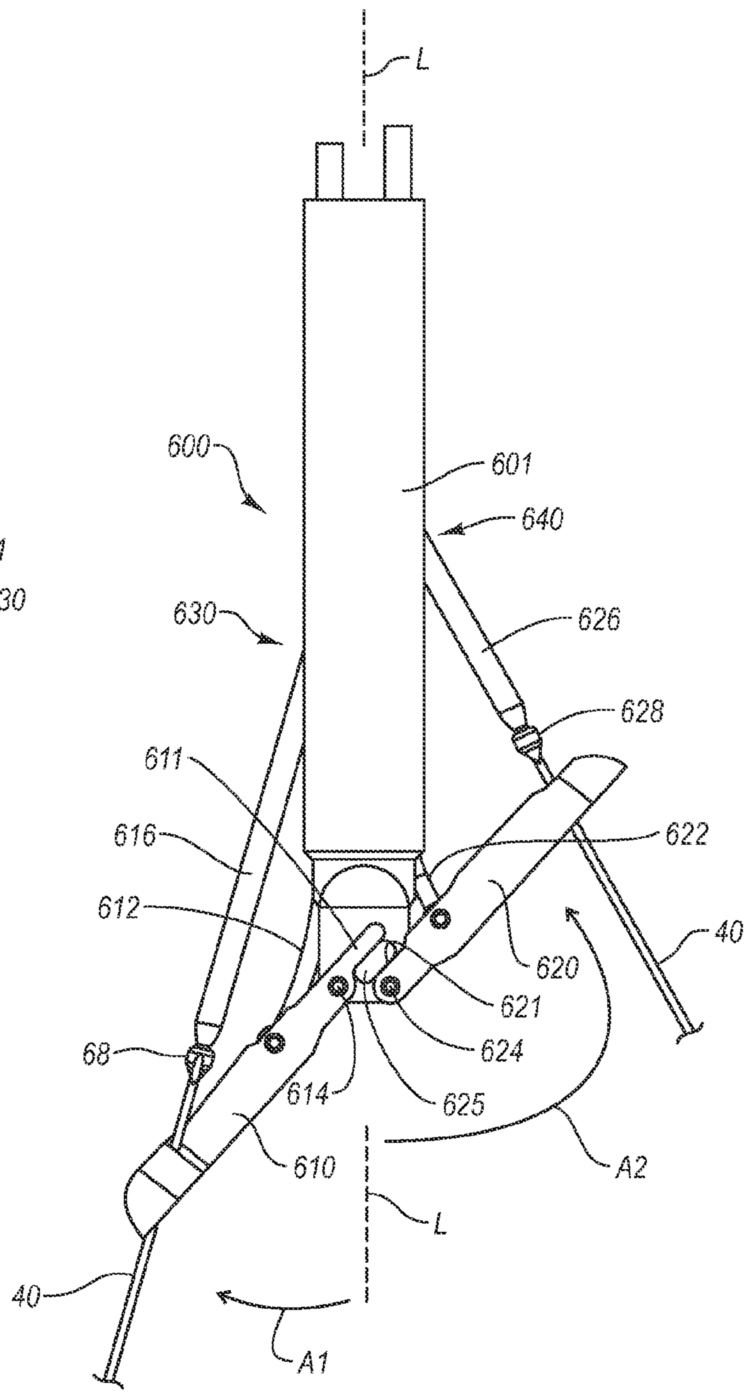
FIG. 5B is a right side elevation view of the present invention after deployment.
Figure 6:
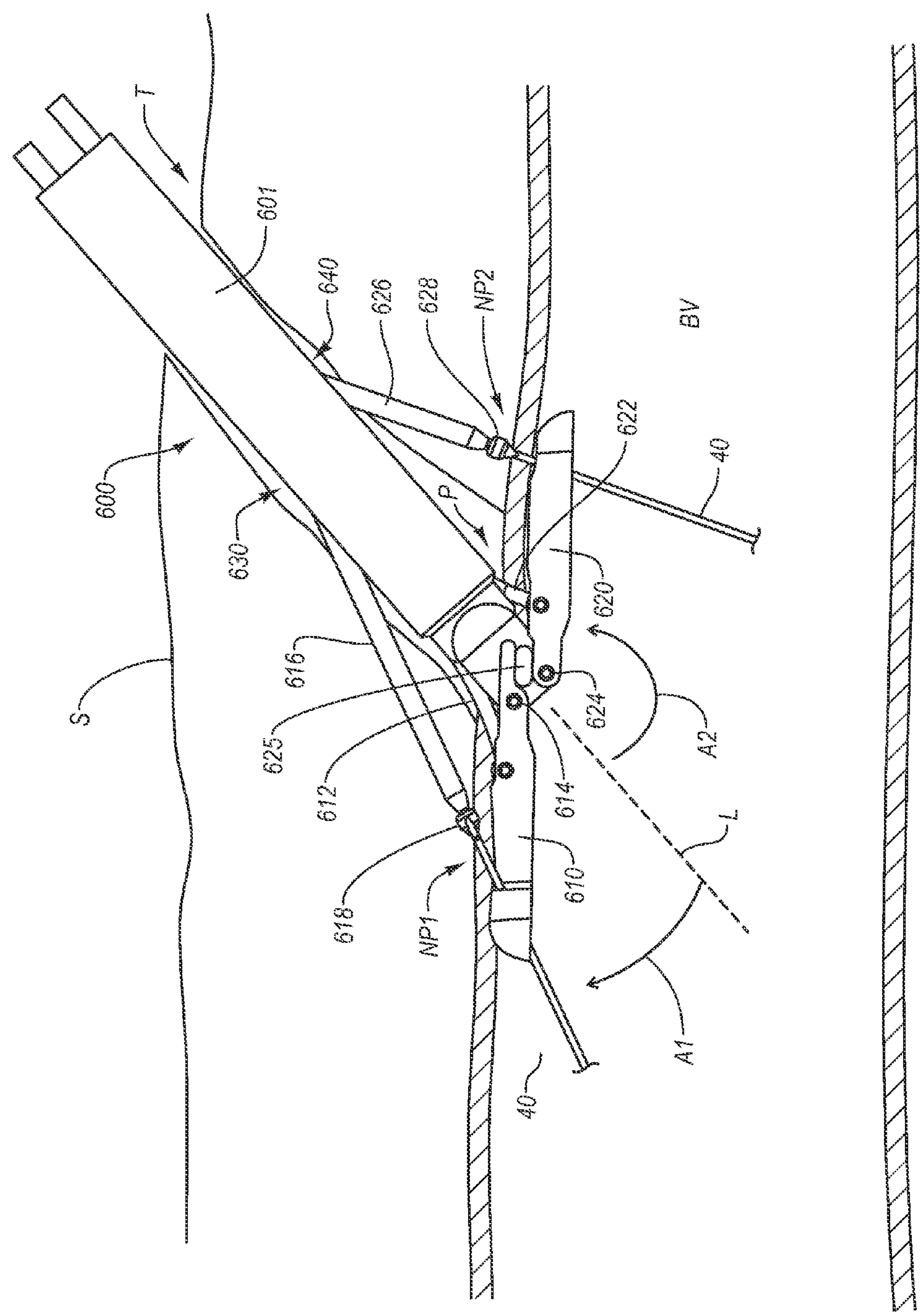
FIG. 6 is an illustration of the system of FIG. 5B deployed at a non perpendicular angle relative to the axis of a blood vessel while the first and second arms 610 and 620 are positioned longitudinally along the inside of the wall of blood vessel.

Anterior arm 610 and posterior arm 620 may be made independently moveably by any of a variety of mechanisms, all keeping within the scope of the present invention. In the illustrated embodiments, arms 610 and 620 are independently actionable (i.e. moveable between compact and deployed positions) by flexible linkages in tension or compression. It is to be understood, however, that any push pull wire, gear or cam system, or any other suitable actuation system may be used, all keeping within the scope of the present invention. As illustrated in FIG. 5B, arm 610 may be deployed by moving linkage 612, and arm 620 may be deployed by moving linkage 622. Specifically, by pulling linkage 612 proximally, anterior arm 610 rotates around pivot 614 until finger 611 contacts pivot stop 625. Similarly, by pulling linkage 622 proximally, posterior arm 620 rotates (in an opposite direction) around pivot 624 until stop surface 621 contacts pivot stop 625. Specifically, anterior arm 610 moves through angle A1 when moved from its compact position to its deployed position. Referring to FIG. 6, posterior arm 620 moves through angle A2 when moved from its compact position to its deployed position. As can be appreciated, by instead distally pushing linkages 612 and 622, arms 610 and 620 can be moved back to their compact (i.e.: non-deployed) position.

After deploying arms 610 and 620 (by retracting linkages 612 and 622) a first needle 616, and a second needle 626 can then be advanced toward the distal ends of arms 610 and 620, respectively to retrieve opposite ends of a suture 40. In various embodiments, needles 616 and 626 are longitudinally advanceable along the shaft 601 of suturing device 600, and exit through side wall openings 630 and 640 at locations proximal to the arms 610 and 620, respectively.

FIG. 6 shows an embodiment of the present invention deployed at a non perpendicular angle relative to the axis of a blood vessel BV while the anterior arm 610 and posterior arm 620 are positioned longitudinally along the inside of the wall of blood vessel BV. Specifically, the distal end of suturing device 600 is positioned though a puncture P in blood vessel BV.

Needles 616 and 626 are advanced longitudinally along through shaft, and exit through side wall openings 630 and 640, and then puncture through respective needle punctures NP1 and NP2 in the wall of blood vessel BV. Thereafter, needles 616 and 626 can be retracted pulling the opposite ends of suture 40 upwardly through punctures NP1 and NP2 in the wall of blood vessel BV.

In various embodiments, cuffs 618 and 628 can be provided at opposite ends of suture 40 to ensure that the distal ends of needles 616 and 626 connect securely onto the opposite ends of suture 40. Various embodiments of cuffs, links, barbs, fasteners, or combinations thereof are also contemplated to ensure that the distal ends of needles 616 and 626 connect securely onto the opposite ends of suture 40. Thus, cuffs 618 and 628 may be any of a variety of different designs.

Referring again to FIGS. 5A and 5B, by moving linkages 612 and 622 independently, and to different distances, arms 610 and 620 may be independently deployed to different angles relative to the longitudinal axis L of the body of suturing device 600. For example, as shown in FIGS. 5A and 5B, arm 610 may be rotated less than 90 degrees from the axis of the elongated body of suturing device 600, whereas 620 may be rotated more than 90 degrees from the axis of the elongated body of suturing device 600.

As shown in FIG. 6, this advantageously allows the elongated body of suturing device 600 to be positioned through tissue Tract T (entering through skin S) at a non-perpendicular angle relative to the axis of a blood vessel BV while the first and second arms 610 and 620 are positioned longitudinally along the inside of the wall of blood vessel BV for placement of the suture axially along the blood vessel and across the puncture. Specifically, suturing device 600 can be used to position the ends of suture 40 at locations such that they can be retrieved by needles 616 and 626, and pulled upwardly through needle punctures NP1 and NP2, respectively.

In various embodiments, the elongated body of suturing device 600 is sufficiently rigid to maintain alignment of needles 616 and 626 with arms 610 and 620, respectively. As can be seen, in various embodiments, needles 616 and 626 may be of different lengths.

Figure 7:
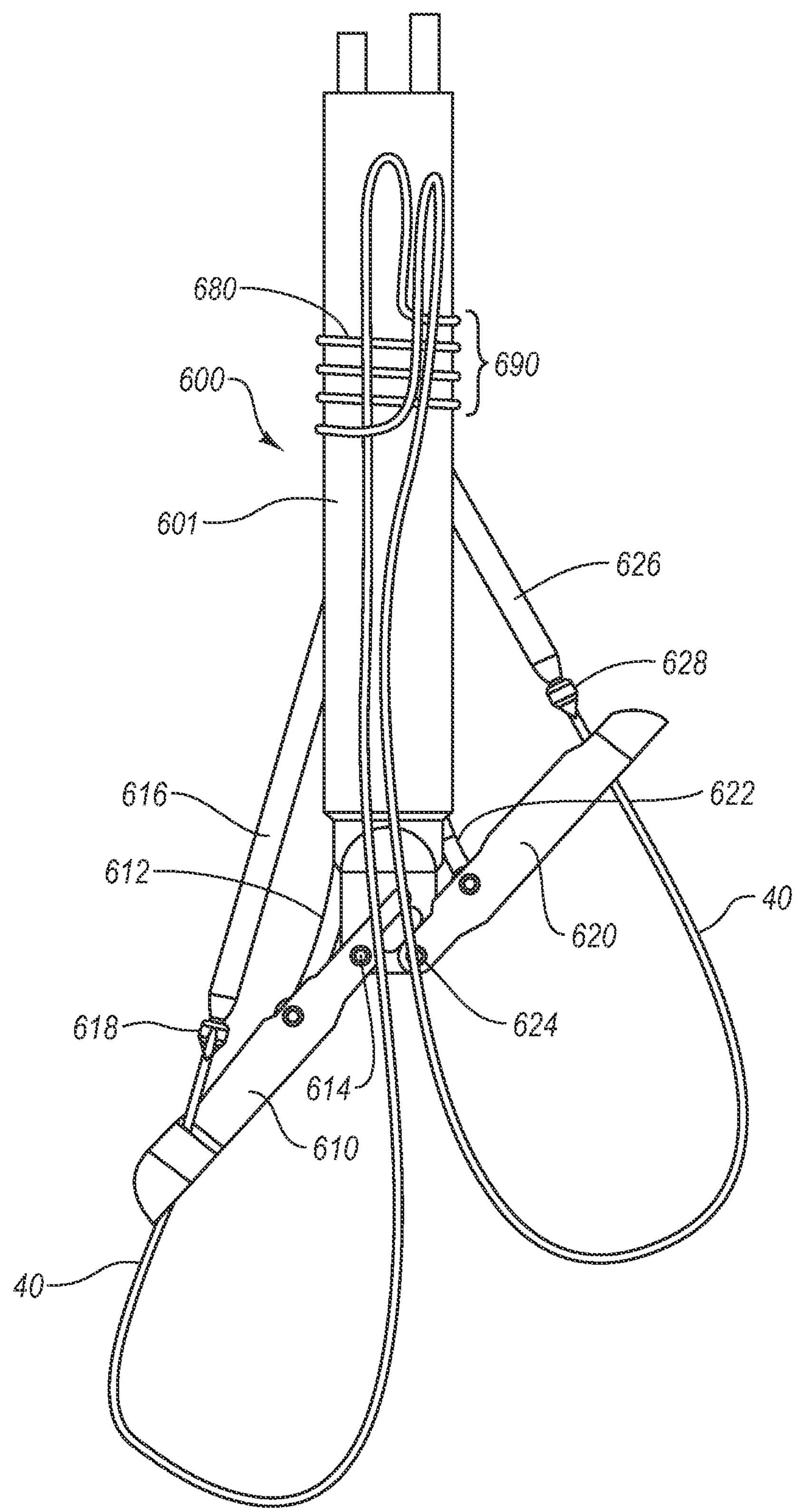
FIG. 7 is an embodiment of the present split arm invention, incorporating a pre-tied knot.

As shown in FIG. 7, a pre-tied knot feature may also be incorporated into suturing device 600. The pre-tied knot may initially be positioned wrapped around an exterior surface of the suturing device. Specifically, a length of suture 40 having opposite ends and a bight 680 of suture therebetween may be provided with bight 680 being disposed around an exterior surface of device 600. Bight 680 may alternately be pre-arranged around one of the needles and within the elongated body.

Bight 680 includes one or more loops of suture that form a pre-tied knot 690 when one or more ends of suture 40 are advanced through bight 680. Bight 680 of suture may be prearranged in any of several configurations on the device. For example, bight 680 may be pre-arranged so as to define a square knot, a clinch knot or a variety of known or new surgical knots.

In various embodiments, suture 40 is arranged to provide the pre-tied knot 680 that automatically travels down from the shaft of the device 600 where it is stored prior to delivery to the tissue wall. In various embodiments, to distinguish the ends of suture 40, during deployment, the ends of the suture may be distinguished from each other by changing the color of one end (e.g. with dye), providing an attachment on one end (e.g. shrink wrap tubing, a bead, etc.) or with the suture itself (e.g. tying a knot in one end).

In accordance with the present invention, suture bight 680 is disposed on the outside surface of device 600, as shown. In this embodiment, suture 40 does not pass through the interior of the device. It should be understood, however, that other embodiments of the invention may include suture 40 and bight 680 stored inside the shaft or housing of the device rather than on the outside. Yet other configurations may include detachable tips and connecting filaments to enable a pre-tied knot.

After needles 616 and 626 retrieve opposite ends of suture 40, and pull these ends of the suture back up through the center of bight 680 to define the pre-tied knot 690, and arms 610 and 620 are rotated back to a non-deployed position, device 600 may be removed from the patient. Pre-tied knot 690 will slide down the shaft, resulting in a suture pattern in which the opposite ends of suture 40 pass upwardly through the center of bight 680.

While embodiments and applications of this invention have been shown and described, it will be apparent to those skilled in the art that various modifications are possible without departing from the scope of the invention. It is, therefore, to be understood that within the scope of the appended claims, this invention may be practiced otherwise than as specifically described.

What is claimed:

1. An apparatus for suturing a puncture in a blood vessel, comprising:

an elongated body;

a first arm movably connected to the elongated body, the first arm being selectively movable between a retracted position and an extended position, the first arm being positioned in a generally anterior direction relative to the elongated body in the extended position;

a second arm movably connected to the elongated body, the second arm being selectively movable between a retracted position and an extended position, the second arm being positioned in a generally posterior direction relative to the elongated body in the extended position;

at least one needle being selectively extendable from the elongated body to engage at least one needle receiving portion in at least one of the first arm and the second arm.

2. The device of claim 1, wherein the arms are independently deployable.

3. The device of claim 1, further comprising: a first deployment linkage connected to the first arm; and a second deployment linkage connected to the second arm.

4. The device of claim 3, wherein each deployment linkage comprises a member that is pulled proximally to deploy one of the arms, and is pushed distally to move the arm to the compact position.

5. The device of claim 3, wherein each deployment linkage comprises a wire.

6. The device of claim 1, further comprising: a pivot stop on the distal end of the elongated shaft, wherein the pivot stop limits rotation of the arms when they reach the deployed position.

7. The device of claim 6, wherein the at least two arms comprise an anterior arm and a posterior arm, wherein the anterior arm has an extension portion that contacts the pivot stop when the anterior arm is in its deployed position, and wherein the posterior arm has a stop surface that contacts the pivot stop when the posterior arm is in its deployed position.

8. An apparatus for suturing a puncture in a blood vessel, comprising:

an elongated body;

a first arm movably connected to the elongated body, the first arm being selectively movable between a retracted position and an extended position, the first arm being rotatable from the retracted position to the extended position through a first angle;

a second arm movably connected to the elongated body, the second arm being selectively movable between a retracted position and an extended position, the second arm being rotatable from the retracted position to the extended position through a second angle, the second angle being greater than the first angle;

at least one needle being selectively extendable from the elongated body to engage at least one needle receiving portion in at least one of the first arm and the second arm.

9. The apparatus of claim 8, wherein one needle is adapted to be connected to a first end of a length of suture, the suture having a second end and a bight between the first and second ends, the bight being prearranged on the elongate body to define a pre-tied knot when the first end of the suture passes through the bight.

10. The apparatus of claim 8, wherein the elongated body is sufficiently rigid to maintain alignment of the first needle with the first arm and the second needle with the second arm, respectively.

11. The apparatus of claim 8, wherein the first and second end portions of the suture have cuffs disposed thereon.

12. An apparatus for suturing a puncture in a blood vessel, comprising:

an elongated body having a longitudinal axis;

a first arm movably connected to the elongated body, the first arm being selectively movable between a retracted position and an extended position, the first arm being oriented at a non-perpendicular angle relative to the longitudinal axis when the first arm is in the extended position;

a second arm movably connected to the elongated body, the second arm being selectively movable between a retracted position and an extended position, the second arm being oriented at a non-perpendicular angle relative to the longitudinal axis when the first arm is in the extended position, the second arm also being oriented generally parallel to the first arm when the first arm and second arm are in the extended positions;

at least one needle being selectively extendable from the elongated body to engage at least one needle receiving portion in at least one of the first arm and the second arm.

13. The device of claim 12, wherein the at least two arms comprise: a first arm that is pivoted less than 90 degrees to the longitudinal axis of the elongated shaft when in the deployed position; and a second arm that is pivoted more than 90 degrees to the longitudinal axis of the elongated shaft when in the deployed position.

14. The device of claim 12, further comprising: a first deployment linkage connected to the first arm; and a second deployment linkage connected to the second arm.

15. The device of claim 14, wherein each deployment linkage comprises a member that is pulled proximally to deploy one of the arms, and is pushed distally to move the arm to the compact position.

16. The device of claim 14, wherein each deployment linkage comprises a wire.

17. The device of claim 12, further comprising a pivot stop on the distal end of the elongated shaft, wherein the pivot stop limits rotation of the arms when they reach the deployed position.

18. The device of claim 17, wherein the at least two arms comprise an anterior arm and a posterior arm, wherein the anterior arm has an extension portion that contacts the pivot stop when the anterior arm is in its deployed position, and wherein the posterior arm has a stop surface that contacts the pivot stop when the posterior arm is in its deployed position.

19. An apparatus for suturing a puncture in a blood vessel, comprising:

an elongated body having a first side wall opening and a second side wall opening, the second sidewall opening being longitudinally offset from the first side wall opening;

a first arm movably connected to the elongated body, the first arm being selectively movable between a retracted position and an extended position, the first arm being positioned in a generally anterior direction relative to the elongated body in the extended position;

a second arm movably connected to the elongated body, the second arm being selectively movable between a retracted position and an extended position, the second arm being positioned in a generally posterior direction relative to the elongated body in the extended position;

a first needle being selectively extendable from the elongated body through the first side wall opening and toward the first arm when the first arm is in the extended position; and a second needle being selectively extendable from the elongated body through the second side wall opening and toward the second arm when the second arm is in the extended position.

20. The apparatus of claim 19, wherein the elongated body has a longitudinal axis, the first needle extends from the first side wall opening at a first angle relative to the longitudinal axis, and the second needle extends from the second side wall opening at a second angle relative to the longitudinal axis, the second angle being greater than the first angle.

* * * * *